United States Patent
Midorikawa

(10) Patent No.: US 9,801,759 B2
(45) Date of Patent: Oct. 31, 2017

(54) INTRAOCULAR LENS INSERTION TOOL AND POSITIONING MEMBER PROVIDED IN INTRAOCULAR LENS INSERTION TOOL

(71) Applicant: KOWA COMPANY, LTD., Aichi (JP)

(72) Inventor: Genyo Midorikawa, Nagoya (JP)

(73) Assignee: Kowa Company, Ltd., Aichi (JP)

( * ) Notice: Subject to any disclaimer, the term of this patent is extended or adjusted under 35 U.S.C. 154(b) by 53 days.

(21) Appl. No.: 14/411,075

(22) PCT Filed: Jun. 28, 2013

(86) PCT No.: PCT/JP2013/067933
§ 371 (c)(1),
(2) Date: Dec. 23, 2014

(87) PCT Pub. No.: WO2014/003186
PCT Pub. Date: Jan. 3, 2014

(65) Prior Publication Data
US 2015/0157500 A1     Jun. 11, 2015

(30) Foreign Application Priority Data

Jun. 29, 2012  (JP) .................................. 2012-147692

(51) Int. Cl.
*A61F 2/16* (2006.01)
*A61F 9/007* (2006.01)

(52) U.S. Cl.
CPC .......... *A61F 9/00736* (2013.01); *A61F 2/167* (2013.01); *A61F 2/1678* (2013.01)

(58) Field of Classification Search
CPC .......... A61F 2/16; A61F 2/167; A61F 2/1662; A61F 2/1678; A61F 9/007; A61F 9/00
See application file for complete search history.

(56) References Cited

U.S. PATENT DOCUMENTS

| 8,123,804 | B2 | 2/2012 | Tanaka |
| 8,152,817 | B2 * | 4/2012 | Tanaka .................. A61F 2/1664 606/107 |

(Continued)

FOREIGN PATENT DOCUMENTS

| CN | 101467926 | 7/2009 |
| CN | 101511309 | 8/2009 |

(Continued)

OTHER PUBLICATIONS

International Preliminary Report on Patentability dated Jan. 8, 2015 in PCT Application No. PCT/JP2013/067933.

(Continued)

*Primary Examiner* — Victor Nguyen
(74) *Attorney, Agent, or Firm* — Knobbe Martens Olson & Bear LLP

(57) ABSTRACT

Provided is a configuration in which when a positioning member is removed from an intraocular lens insertion tool, restrictions on the position and posture of an intraocular lens can be lifted smoothly without exerting influence on the intraocular lens and the insertion tool itself. The present invention is provided with: an approximately cylindrical nozzle body (10); a stage part which is provided in the nozzle body (10) and houses an intraocular lens; a plunger which presses the intraocular lens housed in the stage part by the forward end thereof to discharge the intraocular lens into an eyeball; and a positioning member (60) which restricts the initial position and posture of the intraocular lens by being mounted to the stage part from the outside. Rib sections (12g) are formed so as to extend in the front-back direction of the nozzle body (10) at the outer periphery of the stage part, and side wall parts (51, 51) and rotation prevention wall parts (59, 59) are formed in the positioning member (60) so as to sandwich the rib sections (12g, 12g)

(Continued)

from both sides, thereby restricting the rotation of the positioning member (60) with respect to the stage part.

18 Claims, 14 Drawing Sheets

(56)  References Cited

U.S. PATENT DOCUMENTS

| 2005/0182419 | A1* | 8/2005 | Tsai ..................... A61F 2/1648 606/107 |
| 2009/0171365 | A1 | 7/2009 | Tanaka |
| 2010/0130985 | A1 | 5/2010 | Tanaka |
| 2012/0253356 | A1 | 10/2012 | Niwa et al. |

FOREIGN PATENT DOCUMENTS

| EP | 2255751 | 12/2010 |
| JP | 2006-181269 | 7/2006 |
| JP | 2008-061677 | 3/2008 |
| JP | 2009160138 | 7/2009 |
| JP | 2010-273986 | 12/2010 |
| WO | WO 2006/070561 | 7/2006 |
| WO | 2011061791 | 5/2011 |

OTHER PUBLICATIONS

Extended European Search Report dated Feb. 29, 2016 in the corresponding European Patent Application No. 13809051.9.
Office Action dated Dec. 2, 2015 in corresponding Chinese Patent Application No. 201380034524.6.
Office Action dated Jan. 23, 2017 in corresponding Chinese Patent Application No. 201380034524.6.
Office Action dated May 9, 2017 in corresponding Japanese Patent Application No. 2014-522712.
Decision on Rejection (with partial English translation) for Chinese Application No. 201380034524.6 dated May 22, 2017 (12 Pages).

* cited by examiner

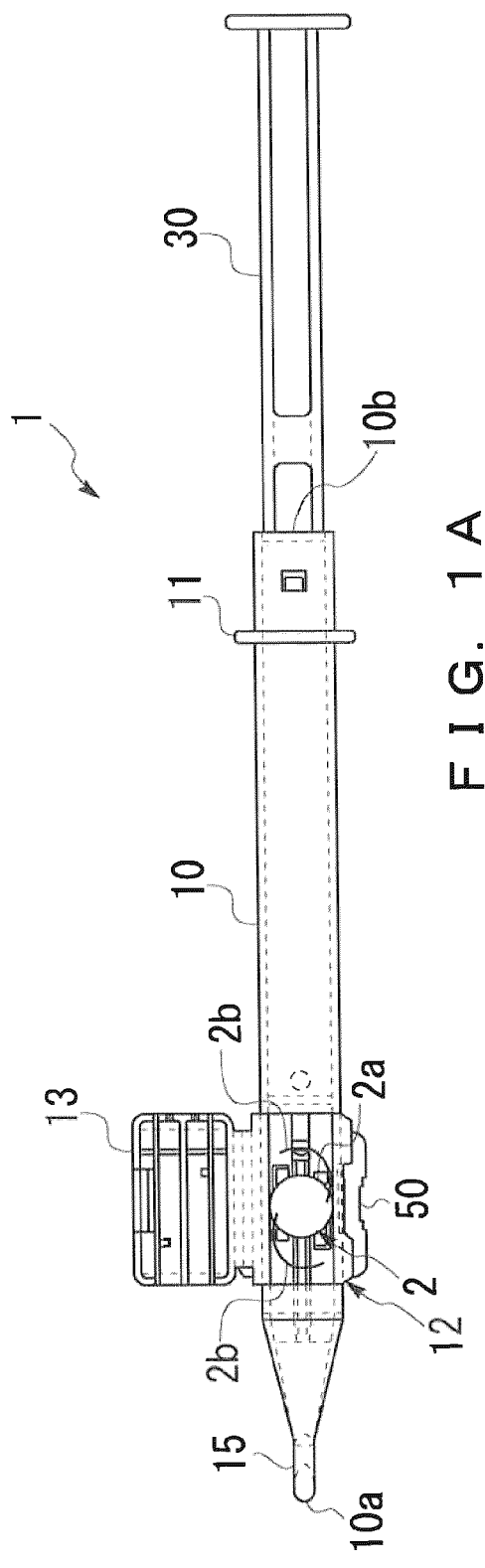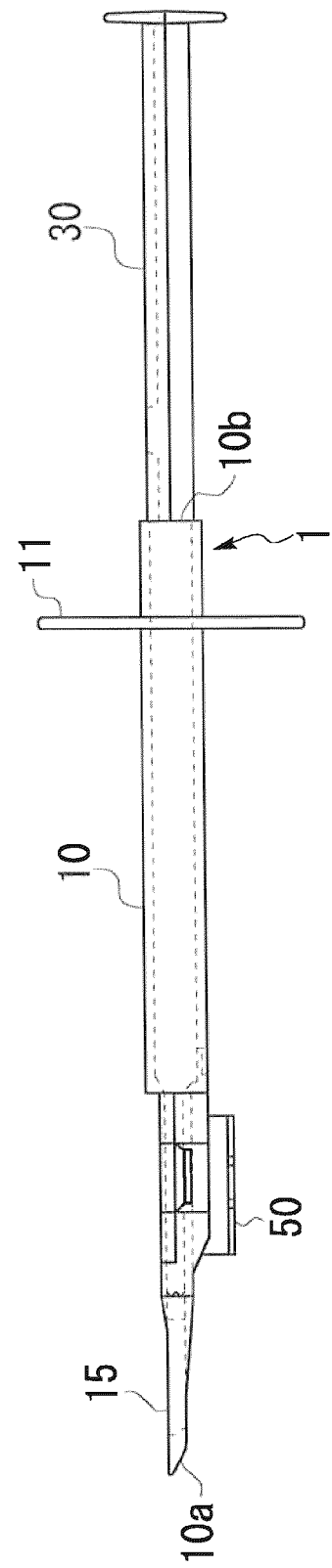
FIG. 1A
FIG. 1B

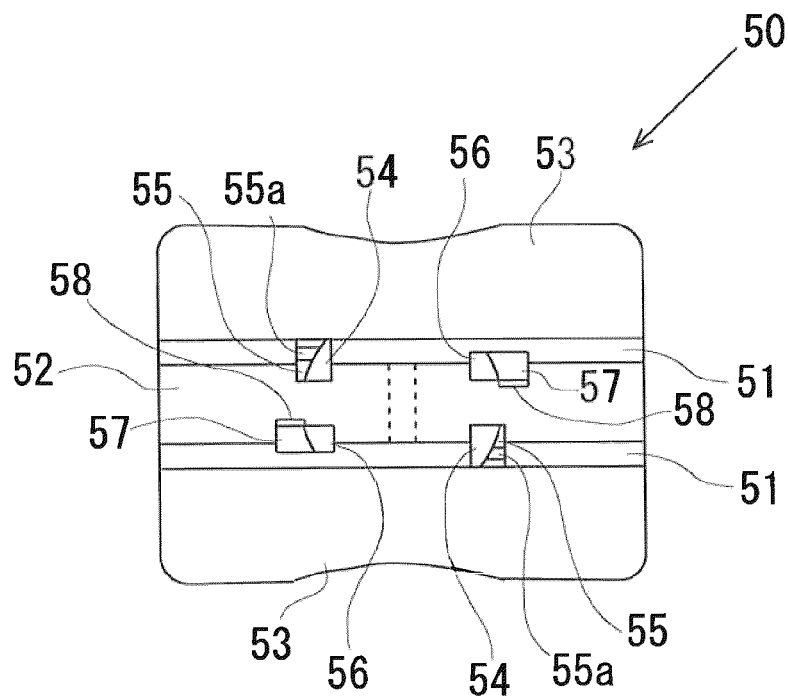
F I G. 4 A
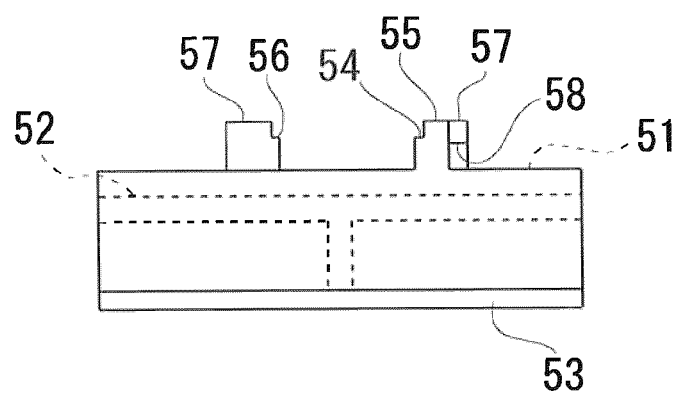
F I G. 4 B

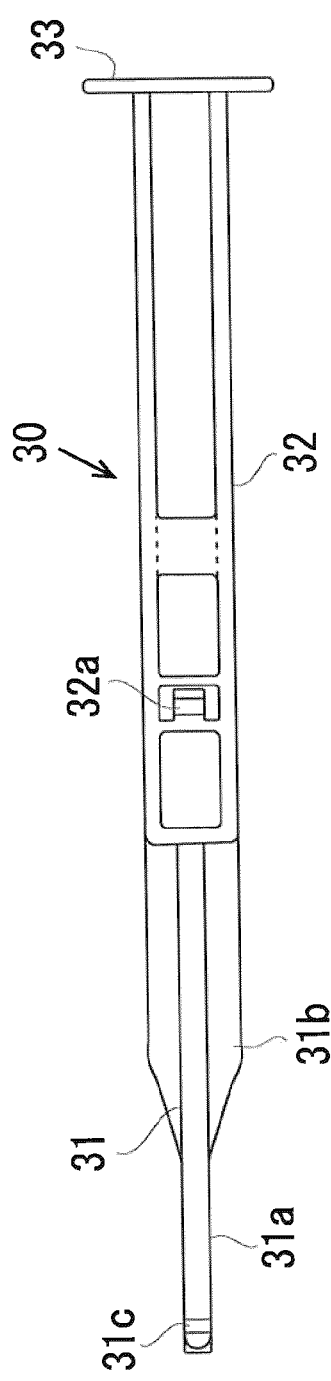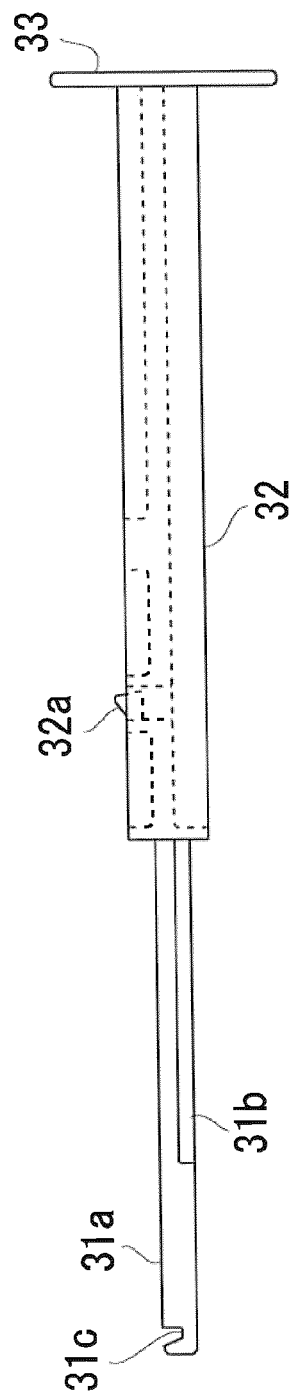
F I G. 5 A
F I G. 5 B

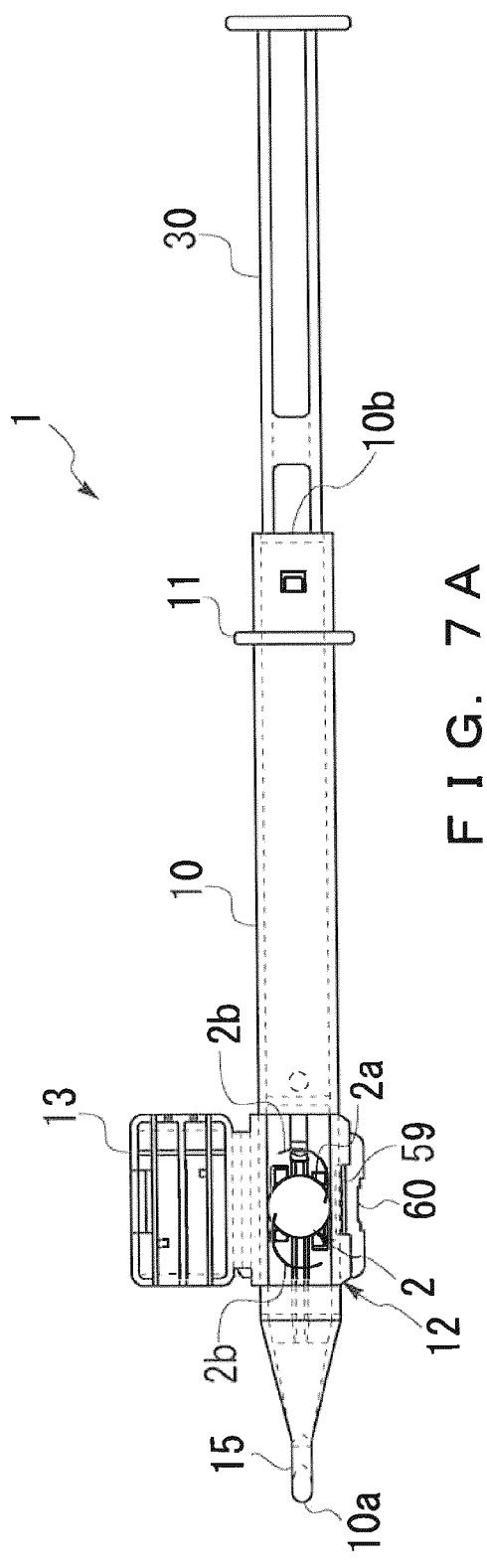
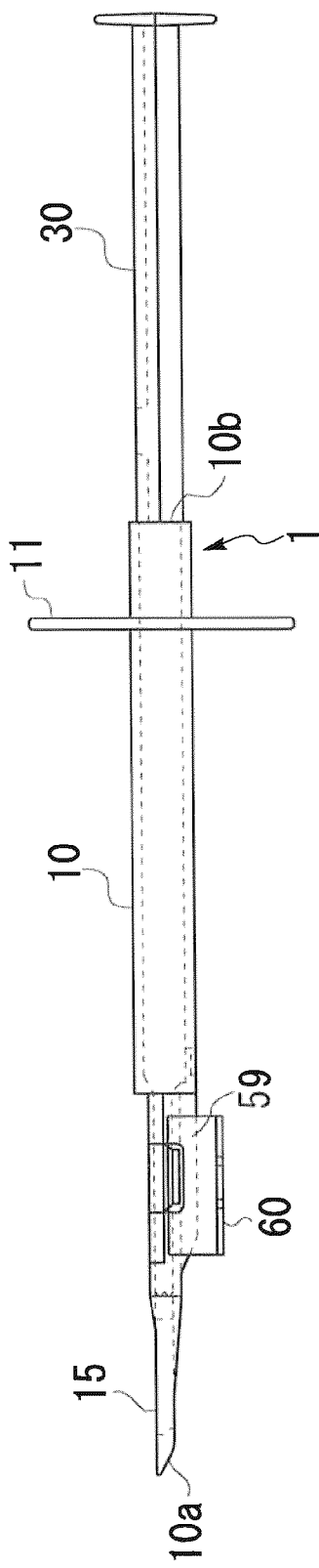
FIG. 7A
FIG. 7B

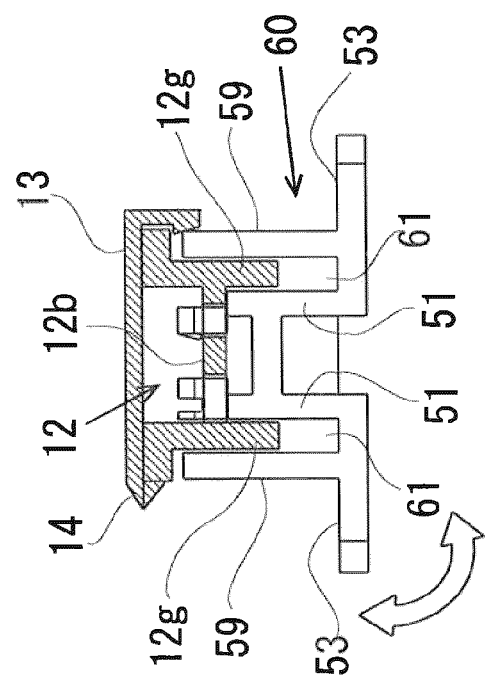
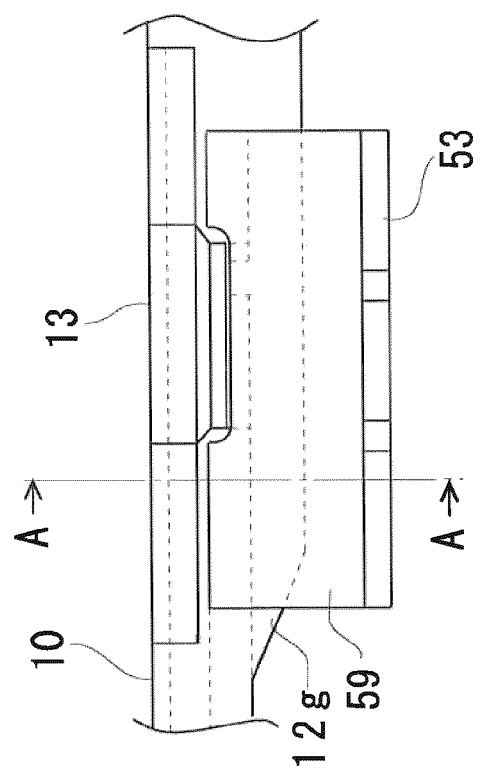
FIG. 8A
FIG. 8B

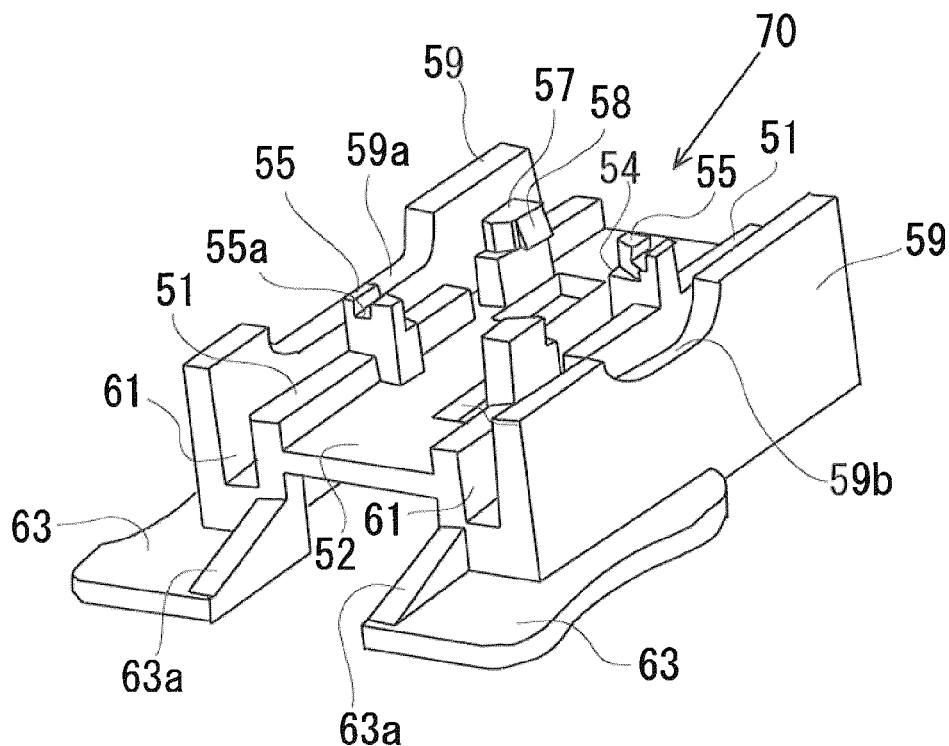
F I G. 1 1 A
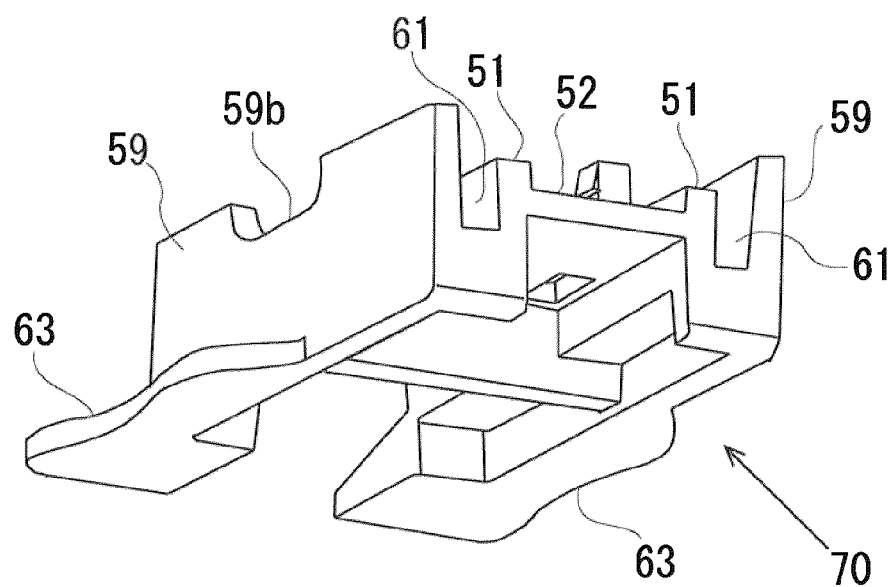
F I G. 1 1 B

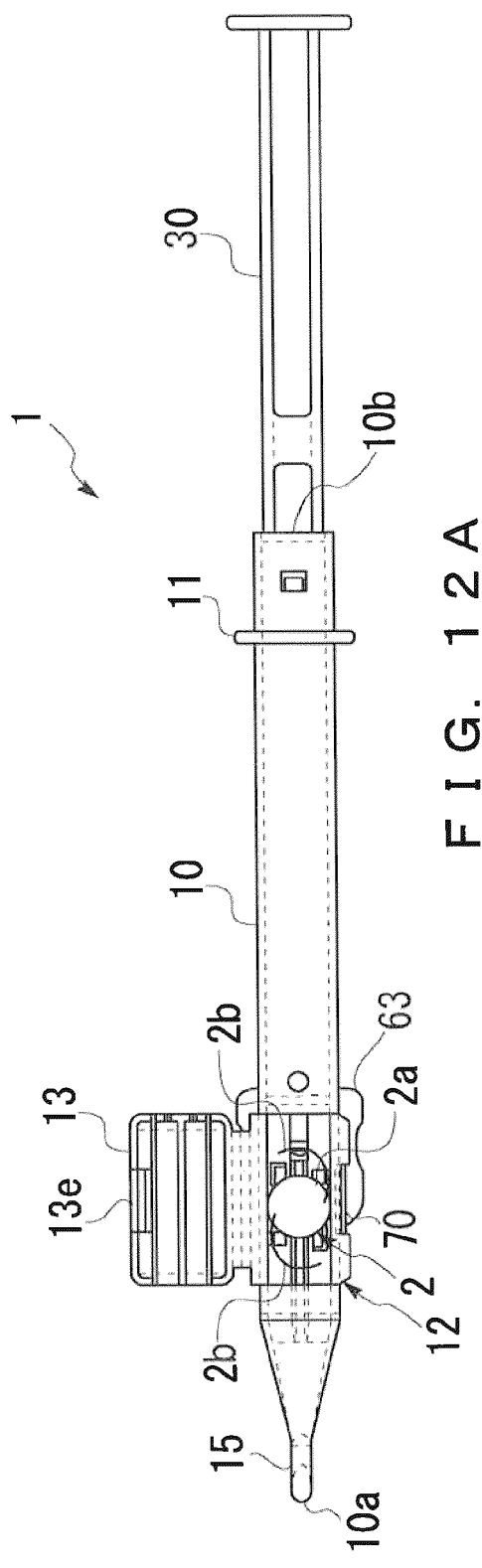
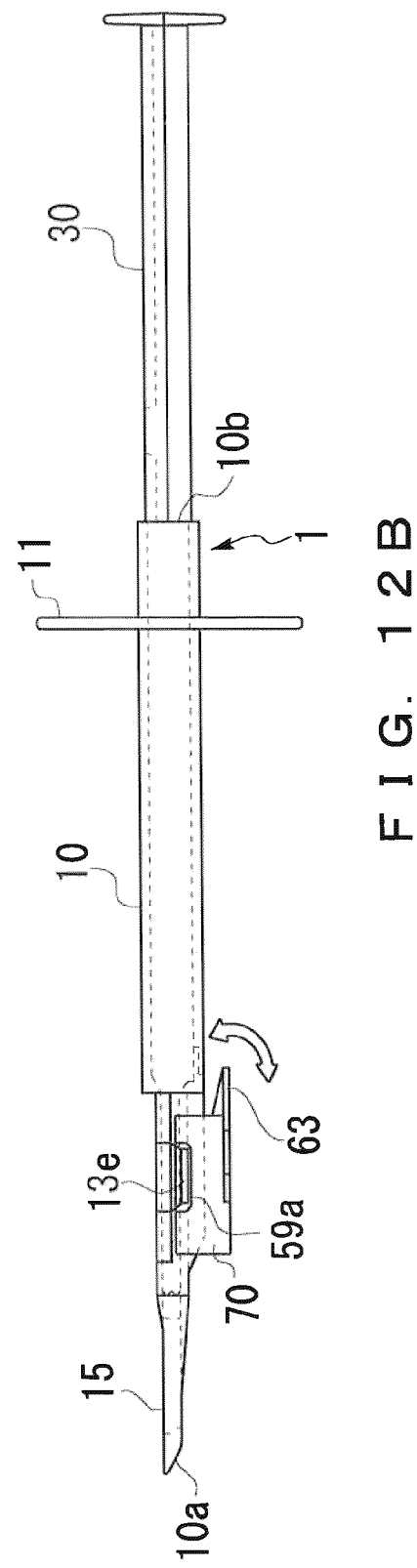
F I G. 12A
F I G. 12B

US 9,801,759 B2

INTRAOCULAR LENS INSERTION TOOL AND POSITIONING MEMBER PROVIDED IN INTRAOCULAR LENS INSERTION TOOL

TECHNICAL FIELD

The present invention relates to an intraocular lens insertion tool for inserting an intraocular lens into an eyeball of a patient, and a positioning member provided in the intraocular lens insertion tool.

BACKGROUND ART

Conventionally, in a surgery such as a cataract, a treatment has been performed in which an incision is provided in an ocular tissue such as a cornea (sclera) in the eyeball and a crystalline lens anterior capsule portion, an intracapsular crystalline lens is extracted and removed via the incision, and thereafter, an intraocular lens substituting the crystalline lens is inserted into the eye and disposed in the capsule from the incision.

Especially, in recent years, when inserting the intraocular lens into the eyeball from the incision, in many cases, an insertion tool as illustrated below is used. That is, a leading end opening of an insertion cylindrical portion provided at a leading end portion of a tool main body is inserted into the eyeball through the incision, and the intraocular lens is extruded from the leading end opening of the insertion cylindrical portion by a rod-shaped plunger in a state of being slightly deformed in the tool main body, thereby inserting the intraocular lens into the eyeball. By using such an insertion tool, since it is possible to simply insert the intraocular lens into the eyeball by the use of the incision formed for extraction and removal of the crystalline lens, it is possible to simplify the surgery, and it is possible to suppress an occurrence of astigmatism and an occurrence of infectious disease after surgery.

Incidentally, some above-described intraocular lens insertion tools have a positioning member that holds the position and posture of the intraocular lens in the insertion tools while restricting them, and hold the intraocular lens using the positioning member in the state before use. In this type of intraocular lens insertion tool, the restrictions on the position and posture of the intraocular lens are released by removing the positioning member during use, and the intraocular lens is set to an extrudable state by the plunger (for example, see Patent Literature 1). In this case, depending on a method of removing the positioning member, an inconvenience has occurred in which a lens main body or a support portion of the intraocular lens are interposed by some parts of the positioning member, in some cases, it is not possible to normally release the restrictions on the position and posture of the intraocular lens, and it is difficult to smoothly perform the inserting operation of the intraocular lens.

CITATION LIST

Patent Literature

Patent Literature 1: JP 2008-61677 A
Patent Literature 2: JP 2010-273986 A

SUMMARY OF INVENTION

Technical Problem

The present invention has been made in view of the above-described conventional problems, and an object thereof is to provide a technique capable of smoothly releasing the restrictions on the position and posture of the intraocular lens without affecting the intraocular lens or the insertion tool itself, when detaching the positioning member from the intraocular lens insertion tool.

Solution to Problem

According to the present invention for solving the above-described problems, there is provided an intraocular lens insertion tool that includes a substantially cylindrical tool main body; a housing portion that is provided in the tool main body to house the intraocular lens; a plunger that discharges the intraocular lens into the eyeball from an insertion cylindrical portion, by pressing the intraocular lens housed in the housing portion by a leading end; and a positioning member that restricts an initial position and posture of the intraocular lens by being mounted to the housing portion from the outside, the intraocular lens insertion tool being a type of being used after detaching the positioning member from the housing portion, wherein in one of an outer circumference of the housing portion or the positioning member, a flat plate portion as a flat plate-shaped wall portion extending in a front and rear direction of the tool main body is formed, and in the other of the outer circumference of the housing portion or the positioning member, a wall surface disposed to interpose the flat plate portion in parallel from both sides is formed, thereby suppressing the rotation of the positioning member around a longitudinal axis with respect to the housing portion.

More particularly, there is provided an intraocular lens insertion tool that includes a tool main body formed in a substantially cylindrical shape that has an insertion cylindrical portion to be inserted into an incision formed in an ocular tissue and a housing portion capable of housing and disposing the intraocular lens; a plunger that moves the intraocular lens inside the tool main body to discharge the intraocular lens into the eyeball from the insertion cylindrical portion, by pressing the intraocular lens housed in the housing portion with a leading end, by being pushed into the tool main body; and a positioning member that restricts an initial position and posture of the intraocular lens within the tool main body by being mounted to the housing portion from the outside, the intraocular lens insertion tool permitting the movement of the intraocular lens and discharging into the eyeball by the plunger, by detaching the positioning member from the housing portion to release the restrictions on the position and posture of the intraocular lens within the tool main body during use, wherein in one of the outer circumference of the housing portion or the positioning member, a flat plate portion as a flat plate-shaped wall portion formed parallel to a direction of movement of the intraocular lens is provided, and in the other of the outer circumference of the housing portion or the positioning member, a rotation suppressing unit for suppressing the rotation of the positioning member with respect to the housing portion by causing two wall surfaces formed parallel to the flat plate portion to face the flat plate portion from both sides is provided.

According to this, it is possible to provide a flat plate portion in one of the outer circumference of the housing portion or the positioning member, and causing the two wall surfaces formed in the other of the outer circumference of the housing portion or the positioning member parallel to the flat plate portion to face the flat plate portion from both sides, thus it is possible to dispose the flat plate portion so as to be interposed between the two wall surfaces. Therefore, for example, it is possible to more reliably suppress the rotation of the positioning member with respect to the housing portion, compared to the case of suppressing the rotation by causing the one wall surface to face the flat plate portion from the one side.

Furthermore, here, the case of causing the two wall surfaces formed parallel to the flat plate portion to face the plate portion from both sides includes the case of causing the two wall surfaces to face the flat plate portion from both sides while keeping a gap, and the case of causing the two wall surfaces to face the flat plate portion from both sides without a gap. The presence or absence of the gap or the dimension of the gap is defined by an angle of rotation allowed for the positioning member. In addition, the direction of rotation capable of being suppressed in this case is mainly the rotation around a direction of movement (an axial direction of the plunger or an axial direction of the tool main body) of the intraocular lens. In addition, the outer circumference of the housing portion in the present invention illustrates an outer surface of the housing portion of the tool main body, and, for example, it may be a surface in a direction in which the positioning member should be attached to the outer surface of the housing portion.

Furthermore, in the present invention, the flat plate portion may be provided on the outer circumference of the housing portion, and the rotation suppressing unit may be provided in the positioning member. Originally, since a rib for securing strength of the housing portion is often provided on the outer circumference of the housing portion, according to the present invention, it is possible to utilize the rib originally provided in the housing portion as the flat plate portion as it is.

Furthermore, in the present invention, the flat plate portion and the rotation suppressing unit may be provided on both sides with respect to the central axis of the direction of movement of the intraocular lens, when viewed from a direction of optical axis of the intraocular lens housed in the housing portion. In that case, it is possible to cause each of the two wall surfaces to face the flat plate portion provided at two positions around the axis in the direction of movement of the intraocular lens from both sides, and it is possible to more reliably suppress the rotation of the positioning member with respect to the housing portion.

Furthermore, in the present invention, the positioning member may have a plurality of convex portions that performs the position restrictions on the intraocular lens, the plurality of convex portions may be inserted into a plurality of holes formed on a placing surface as a surface on which the intraocular lens is placed in the housing portion, and when a locking portion provided on a side surface of the convex portion engages with an end surface of the placing surface forming the hole, the positioning member may be mounted to the housing portion.

In the intraocular lens insertion tool having such a type of the positioning member, since the positioning member rotates around the axis in the direction of movement of the intraocular lens, the convex portion easily interposes the lens main body or the support portion of the intraocular lens, or damages the housing portion. Therefore, by applying the present invention to the intraocular lens insertion tool having such a type of the positioning member, it is possible to make the effect of the invention more remarkable.

Furthermore, in the present invention, the intraocular lens may include a lens main body, and a whisker-like support portion extending outward from the outer circumference of the lens main body, a part of the plurality of convex portions may have a groove portion for supporting the support portion, and the groove portion may be formed parallel to the direction of movement of the intraocular lens.

In such a case, when the positioning member rotates around the axis in the direction of movement of the intraocular lens, in some cases, the groove portion for supporting the support portion is deformed by interference between the convex portion and the housing portion, and interposes the support portion of the intraocular lens. Therefore, by applying the present invention to the intraocular lens insertion tool having such a type of the positioning member, it is possible to suppress the interposition of the support portion of the intraocular lens into the groove portion, and it is possible to make the effect of the invention more remarkable.

Furthermore, in the present invention, the positioning member may have a gripping portion for gripping when attaching or detaching the positioning member to and from the housing portion, and the gripping portion may be provided to be biased from the center in the direction of movement of the intraocular lens in the positioning member.

According to this, when a user detaches the positioning member from the housing portion by gripping the gripping portion, structurally, the positioning member easily rotates around the axis in the direction vertical to the direction of movement of the intraocular lens, and by rotating the positioning member around such an axis, the positioning member can be easily detached from the housing portion. As a result, since there is no need for rotation around the axis in the direction of movement of the intraocular lens, it is possible to more reliably suppress the rotation of the positioning member around the axis in the direction of movement of the intraocular lens.

Furthermore, according to this, when mounting the positioning member to the housing portion, it is possible to suppress mounting in an opposite direction with regard to the direction of movement of the intraocular lens.

Furthermore, in the present invention, an erroneous mounting prevention portion may be formed in at least a part of the wall surface facing the flat plate portion in the rotation suppressing unit, and the erroneous mounting prevention portion prohibits the mounting by interfering with a predetermined portion of the housing portion, when the positioning member is mounted in an opposite direction with regard to the direction of movement of the intraocular lens. According to this, it is possible to more reliably suppress the mounting in the opposite direction with regard to the direction of movement of the intraocular lens when mounting the positioning member to the housing portion.

In addition, the intraocular lens insertion tool of the present invention may be a preset type insertion tool in which the intraocular lens is housed and the positioning member is mounted in the housing portion in advance in the manufacturing process, and which is distributed in a state in which the intraocular lens is housed and the positioning member is mounted in the housing portion. By applying the above-described invention to such a case, it is possible to further improve the reliability of the preset type insertion tool.

Furthermore, the present invention may be a positioning member provided in any one of the above-described intraocular lens insertion tools.

In addition, it is possible to use the above-described means for solving the problems of the present invention in combination as much as possible.

Advantageous Effects of Invention

According to the present invention, when detaching the positioning member from the intraocular lens insertion tool, it is possible to smoothly release the restrictions on the position and posture of the intraocular lens, without affecting the intraocular lens and the insertion tool itself.

BRIEF DESCRIPTION OF DRAWINGS

FIG. 1A and FIG. 1B are diagrams illustrating a schematic configuration of a conventional intraocular lens insertion tool.

FIG. 4A and FIG. 4B are diagrams illustrating a schematic configuration of a conventional positioning member.

FIG. 5A and FIG. 5B are diagrams illustrating a schematic configuration of a plunger.

FIG. 7A and FIG. 7B are diagrams illustrating a schematic configuration of an intraocular lens insertion tool in the first example of the invention.

FIG. 8A and FIG. 8B are diagrams illustrating the vicinity of a positioning member in the intraocular lens insertion tool in the first example of the invention.

FIG. 11A and FIG. 11B are perspective views of the positioning member in the third example of the invention.

FIG. 12A and FIG. 12B are diagrams illustrating a schematic configuration of the intraocular lens insertion tool in the third example of the invention.

DESCRIPTION OF EMBODIMENTS

Figure 2A:
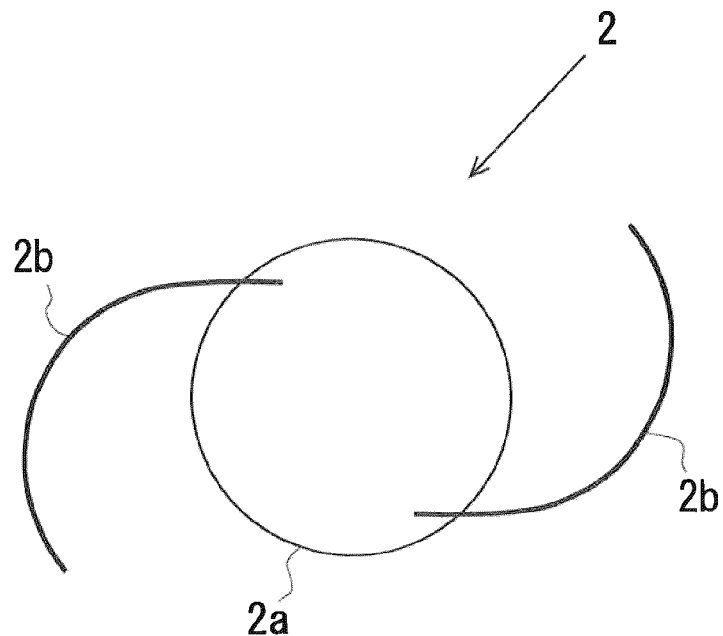
FIG. 2A and FIG. 2B are diagrams illustrating a schematic configuration of an intraocular lens.

Hereinafter, embodiments of the invention will be described by referring to the drawings.

First Example

FIG. 1A and FIG. 1B illustrate schematic configurations of a conventional intraocular lens insertion tool 1 (hereinafter, simply referred to as the insertion tool 1). FIG. 1A illustrates a plan view, and FIG. 1B illustrates a side view. The insertion tool 1 has a nozzle body 10 as a tool main body, and a plunger 30 which is inserted into the nozzle body 10 so as to be able to reciprocate. In the nozzle body 10, one side formed in a cylindrical shape with a substantially rectangular cross-section (hereinafter, a largely open side is referred to as a rear end portion 10b) is largely open, and at an end portion on the other side, a nozzle portion 15 as a thinly narrowed insertion cylindrical portion, and an obliquely open leading end portion 10a are included. In addition, hereinafter, a direction from the leading end portion 10a toward the rear end portion 10b of the nozzle body 10 or its opposite direction (a direction parallel to the direction of movement of the intraocular lens) is set to a front and rear direction, a direction perpendicular to a sheet surface in FIG. 1A is set to a upward and downward direction, and a direction perpendicular to the sheet surface in FIG. 1B is set to a leftward and rightward direction.

In the vicinity of the rear end portion 10b of the nozzle body 10, a hold portion 11 is integrally provided which protrudes in a plate shape and is caught by a finger when a user pushes the plunger 30 to the leading end side of the nozzle body 10. In addition, on the rear end side of the nozzle portion 15 of the nozzle body 10, a stage portion 12 as a housing portion for setting an intraocular lens 2 is provided. The stage portion 12 is configured so that the upper side (a vertical front side of the sheet surface in FIG. 1A)) of the nozzle body 10 is open by opening a stage lid portion 13. Furthermore, a positioning member 50 is mounted to the stage portion 12 from the lower side (a vertical back side of the sheet surface in FIG. 1A) of the nozzle body 10. By this positioning member 50, the position and posture of the intraocular lens 2 are restricted within the stage portion 12 before use (during transport), and the intraocular lens 2 is stably held.

That is, in the insertion tool 1, during manufacture, in a state in which the stage lid portion 13 opens and the positioning member 50 is attached to the stage portion 12, the intraocular lens 2 is set to the stage portion 12. Moreover, after closing the stage lid portion 13, the insertion tool is shipped and sold. Furthermore, during use, the user detaches the positioning members 50 while closing the stage lid portion 13, and then, pushes the plunger 30 to the leading end side of the nozzle body 10. Thus, the intraocular lens 2 is pressed by the plunger 30, and the intraocular lens 2 is extruded from the leading end portion 10a. In addition, the nozzle body 10, the plunger 30, and the positioning member 50 in the insertion tool 1 are formed of a resin material such as polypropylene. Polypropylene is a material that has a proven track record in a medical device and has high reliability such as chemical resistance.

Figure 2B:
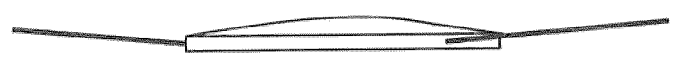

FIG. 2A and FIG. 2B are diagrams illustrating a schematic configuration of the intraocular lens 2. FIG. 2A illustrates a plan view, and FIG. 2A illustrates a side view. The intraocular lens 2 is formed to have a lens main body 2a having a predetermined refractive power, and two whisker-like support portions 2b and 2b that are provided in the lens main body 2a to hold the lens main body 2a within the eyeball. The support portions 2b and 2b correspond to a lens holding portion in this embodiment. The lens main body 2a is formed from a flexible resin material.

Figure 3:
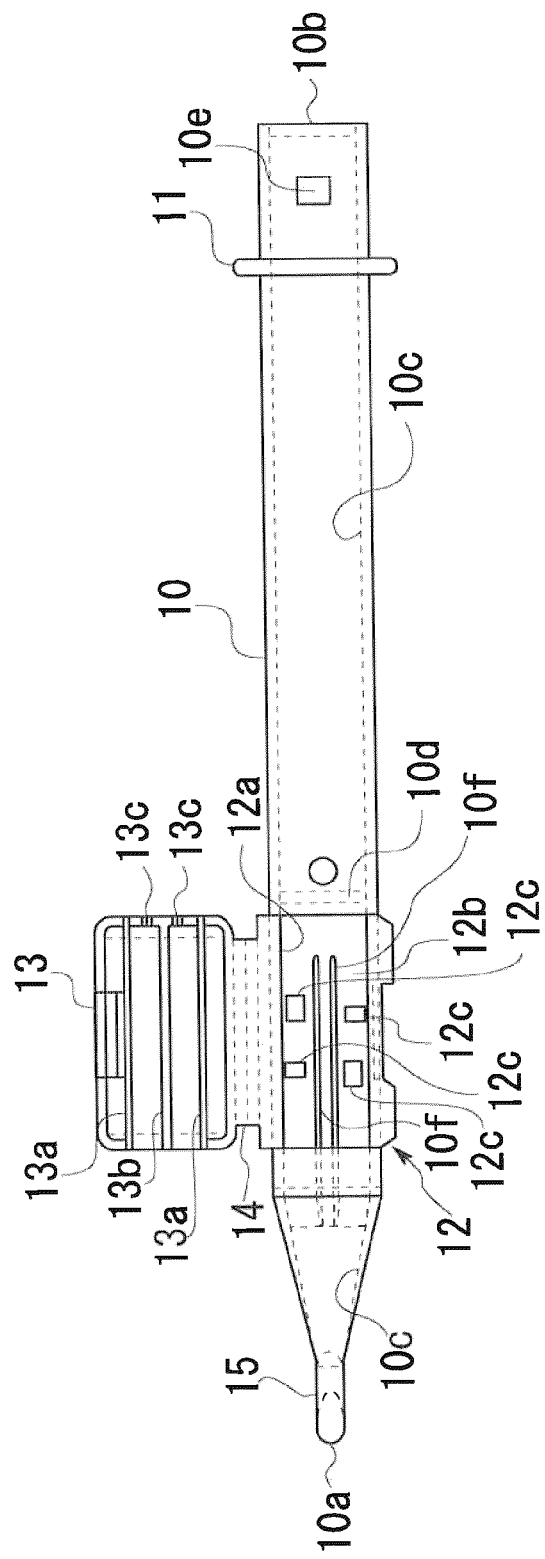
FIG. 3 is a diagram illustrating a schematic configuration of a nozzle body.

FIG. 3 illustrates a plan view of the nozzle body 10. In the nozzle body 10 as described above, the intraocular lens 2 is set to the stage portion 12. Moreover, the intraocular lens 2 is pressed by the plunger 30 in that state and extruded from the leading end portion 10a. In addition, a through hole 10c, in which the cross-sectional shape varies in response to changes in the external form of the nozzle body 10, is provided inside the nozzle body 10. Moreover, when the intraocular lens 2 is extruded, the intraocular lens 2 is deformed in response to changes in the cross-sectional shape of the through hole 10c in the nozzle body 10, is deformed into a shape which easily enters the incision formed in the patient's eyeball, and then is extruded.

The stage portion 12 is formed with a stage groove 12a having a width that is slightly larger than the diameter of the lens main body 2a of the intraocular lens 2. A dimension in the front and rear direction of the stage groove 12a is set to be larger than the maximum width dimension including the support portions 2b and 2b which extend to either side of the intraocular lens 2. Furthermore, a set surface 12b is formed by the bottom surface of the stage groove 12a. A vertical position (a position in a direction perpendicular to the sheet surface of FIG. 3) of the set surface 12b is set above the height position of the bottom surface of the through hole 10c of the nozzle body 10 (front side in the direction perpendicular to the sheet surface of FIG. 3), and the set surface 12b and the bottom surface of the through hole 10c are connected by a bottom inclined surface 10d. In addition, on the set surface 12b, two guide portions 10f and 10f for guiding a cylindrical portion 31a to be described below in the plunger 30 are provided.

The stage portion 12 and the stage lid portion 13 are integrally formed. The stage lid portion 13 has a dimension in the front and rear direction that is equivalent to the stage portion 12. The stage lid portion 13 is connected by a thin plate-shaped connecting portion 14 that is formed by extending the side surface of the stage portion 12 to the stage lid portion 13 side. The connecting portion 14 is flexibly formed in a central portion, and the stage lid portion 13 is adapted to be able to overlap and close the stage portion 12 from the upper side, by bending the connecting portion 14.

In the stage lid portion 13, on a surface facing the set surface 12b during closing, ribs 13a and 13b are provided to reinforce the stage lid portion 13 and stabilize the position of the intraocular lens 2. In addition, a guide projection 13c is provided as an upper guide of the plunger 30.

Below the set surface 12b of the stage portion 12, the positioning member 50 is detachably provided. FIG. 4A and FIG. 4B illustrate schematic configurations of the positioning member 50. FIG. 4A illustrates a plan view, and FIG. 4B illustrates a side view. The positioning member 50 is configured separately from the nozzle body 10, and has a structure in which a pair of side wall portions 51 and 51 is provided perpendicular to a connecting portion 52 on both right and left sides of the plate-shaped connecting portion 52. From the lower end of each side wall portion 51, holding portions 53 and 53 as gripping portions are provided to extend outward and spread.

Moreover, at the diagonal positions in the central portion of the connecting portion 52, a pair of first placing portions 54 and 54 protruding upward is formed. Furthermore, in a portion of the outer circumferential side of the first placing portion 54, first positioning portions 55 and 55 are formed to protrude further upward. An inner wall of the first positioning portion 55 has a circular arc shape, a distance between the inner walls is set to be slightly larger than the diameter dimension of the lens main body 2a of the intraocular lens 1. Also, the first positioning portions 55 and 55 are formed with support portion grooves 55a and 55a as groove portions for receiving the support portions 2b and 2b when placing the intraocular lens 2.

Furthermore, at the diagonal positions opposite to the first placing portions 54 and 54 of the connecting portion 52, a pair of second placing portions 56 and 56 is formed. The height of the top surface of the second placing portion 56 is equal to the height of the top surface of the first placing portion 54. In addition, on the outer portions of the top surfaces of the second placing portions 56 and 56, second positioning portions 57 and 57 are formed to further protrude upward. The inner wall of the second positioning portion 57 also has a circular arc shape, and a distance between the inner walls is set to be slightly larger than the diameter of the lens main body 2a of the intraocular lens 2. In addition, at the end portion of the central side of the connecting portion 52 in the second placing portions 56 and 56, locking claws 58 and 58 are formed to slightly protrude.

In this example, the positioning member 50 is assembled from the lower side of the set surface 12b of the nozzle body 10. On the set surface 12b of the nozzle body 10, a set surface through hole 12c penetrating through the set surface 12b in the thickness direction is formed. The external form of the set surface through hole 12c has an approximately similar shape that is slightly larger than a shape when the first placing portion 54 and the second placing portion 56 of the positioning member 50 are viewed from the top. Moreover, when the positioning member 50 is attached to the nozzle body 10, the first placing portions 54 and 54 and the second placing portions 56 and 56 are inserted into the set surface through hole 12c from the lower side of the set surface 12b, and protrude to the upper side of the set surface 12b.

At that time, the locking claws 58 and 58 provided in the second positioning portions 57 and 57 protrude to the set surface 12b via the set surface through hole 12c, and are locked to the top surface of the set surface 12b. Therefore, the positioning member 50 is assembled from the lower side of the nozzle body 10, the first placing portions 54 and 54 and the second placing portions 56 and 56 are fixed in a state of protruding from the set surface 12b. Moreover, when the intraocular lens 2 is set to the set surface 12b, the outer circumference bottom surface of the lens main body 2a is placed on the top surfaces of the first placing portions 54 and 54 and the second placing portion 56 and 56. In addition, the position of the lens main body 2a is restricted with respect to the horizontal direction, by the first positioning portions 55 and 55 and the second positioning portions 57 and 57. Furthermore, at that time, the vicinity of the base of the support portions 2b and 2b is supported so as to pass through the support portion grooves 55a and 55a, and the rotation around the optical axis of the intraocular lens 2 is restricted. In addition, the first placing portion 54, the second placing portion 56, the first positioning portion 55 and the second positioning portion 57 in this example correspond to the convex portions.

FIG. 5A and FIG. 5B illustrate schematic configurations of the plunger 30. The plunger 30 has a length in the front and rear direction that is slightly larger than the nozzle body 10. Moreover, the plunger is formed from an acting portion 31 of the leading end side based on a cylindrical shape, and an insertion portion 32 of the rear end side based on a rectangular rod shape. Moreover, the acting portion 31 is configured to include a cylindrical portion 31a having a cylindrical shape, and a thin plate-shaped flat portion 31b extending in the leftward and rightward direction of the cylindrical portion 31a.

At the leading end portion of the acting portion 31, a notch portion 31c is formed. As can be seen from FIG. 5A and FIG. 5B, the notch portion 31c is formed in a groove shape that opens in the upward direction and passes in the leftward and rightward direction of the acting portion 31. Also, as can be seen from FIG. 5B, the groove wall of the leading end side of the notch portion 31c is formed by the inclined surface toward the upper part as it goes to the leading end side of the acting portion 31.

Meanwhile, the insertion portion 32 has a generally H-shaped cross-section as a whole, the dimensions thereof in the upward and downward direction and the leftward and rightward direction are set to be slightly smaller than the through hole 10c of the nozzle body 10. In addition, at the rear end of the insertion portion 32, a disk-shaped pressing plate portion 33 extending in the upward, downward, leftward and rightward direction the vertical and horizontal directions is formed.

In a portion of the leading end side from the center in the front and rear direction of the insertion portion 32, a claw portion 32a is formed which protrudes toward the upper side of the insertion portion and is vertically movable by elasticity of the material of the plunger 30. Moreover, when the plunger 30 is inserted into the nozzle body 10, a locking hole 10e illustrated in FIG. 3 provided in the thickness direction on the top surface of the nozzle body 10 engages with the claw portion 32a, and thus, the relative position between the nozzle body 10 and the plunger 30 in the initial state is determined. In addition, the formation positions of the claw portion 32a and the locking hole 10e are set so that, in the engaged state, the leading end of the acting portion 31 is positioned behind the lens main body 2a of the intraocular lens 2 set on the stage portion 12, and is positioned at a location where the notch portion 31c can support the rear support portion 2b of the lens main body 2a from the lower side.

Prior to use of the insertion tool 1 configured as described above, the plunger 30 is inserted into the nozzle body 10 and disposed at the initial position. Furthermore, as described above, the positioning member 50 is attached to the nozzle body 10 from the lower side of the set surface 12b. Thus, the first placing portion 54 and the second placing portion 56 of the positioning member 50 are held in a state that protrudes from the set surface 12b.

Next, the lens main body 2a of the intraocular lens 2 is placed and positioned on the top surfaces of the first placing portion 54 and the second placing portion 56 in the state of causing the support portions 2b and 2b to face in the front and rear direction of the nozzle body 10. In this state, since the outer circumferential portion of the lens main body 2a in the intraocular lens 2 comes into contact with the first placing portion 54 and the second placing portion 56, the central portion is supported in a non-load state. Also, in this state, the support portion 2b of the intraocular lens 2 is also supported by the bottom surface of the notch portion 31c of the plunger 30, other than the support portion grooves 55a and 55a.

When the intraocular lens 2 is inserted into the eyeball using the insertion tool 1, first, the positioning member 50 is detached from the nozzle body 10. Thus, the first placing portion 54 and the second placing portion 56 supporting the lens main body 2a of the intraocular lens 2 are retracted from the set surface 12b, the intraocular lens 2 is movably placed on the set surface 12b, and the restrictions on the position and posture of the intraocular lens 2 are released.

Subsequently, the leading end portion 10a of the nozzle portion 15 of the nozzle body 10 is inserted into the incision provided in the eye tissue. Here, since the leading end portion 10a has an oblique opening shape, it is possible to easily perform the insertion into the incision. Moreover, after inserting the nozzle portion 15 into the incision, in that state, the pressing plate portion 33 of the plunger 30 is pushed to the leading end side of the nozzle body 10. Thus, the leading end of the acting portion 31 of the plunger 30 abuts against the outer circumference of the lens main body 2a of the intraocular lens 2 set on the set surface 12a, and the intraocular lens 2 moves toward the leading end portion 10a along with the advancement of the plunger 30.

Moreover, when the intraocular lens 2 is pressed by the plunger 30 and the nozzle body 10 moves forward, the intraocular lens 2 is deformed in response to changes in the cross-sectional shape of the through hole 10c, the intraocular lens 2 is extruded into the eyeball from the leading end portion 10a of the nozzle body 10 in the deformed state.

Here, in the above-described inserting operation of the intraocular lens 2, when the positioning member 50 is detached from the nozzle body 10, in a case where the positioning member 50 is detached straight in the direction of the optical axis of the intraocular lens 2, in particular, no problems occur. However, for example, when it is detached by twisting so as to rotate around the axis in the front and rear direction (the axis in the direction of movement of the intraocular lens 2) of the insertion tool 1, there is a risk of damage to the nozzle body 10 or the positioning member 50 by interference of the first placing portion 54 and the second placing portion 56 with the end surface of the set surface through hole 12c. In addition, there is a fear that the first placing portion 54 and the second placing portion 56 interpose the lens main body 2a or the support portion 2b of the intraocular lens 2.

In particular, in a case where the right and left outer walls of the first positioning portions 55 and 55 of the first placing portions 54 and 54 are deformed by interference with the end surface of the set surface through hole 12c, in some cases, the support portion grooves 55a and 55a are crushed and the opening portion is closed, and the support portions 2b and 2b are interposed between the support portion grooves 55a and 55a. Then, when the positioning member 50 is detached from the stage portion 12, a situation occurs in which the support portions 2b and 2b of the intraocular lens 2 protrude outside of the set surface through holes 12c, and in some cases, the intraocular lens 2 is damaged, and the insertion intraocular lens 2 becomes impossible.

Figure 6A:
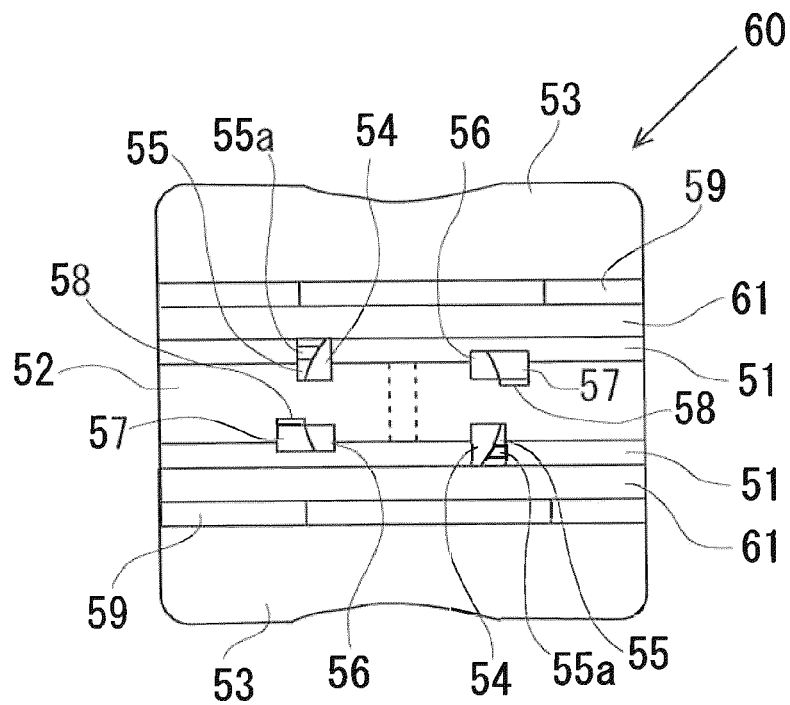
FIG. 6A and FIG. 6B are diagrams illustrating a schematic configuration of the positioning member in a first example of the present invention.
Figure 6B:
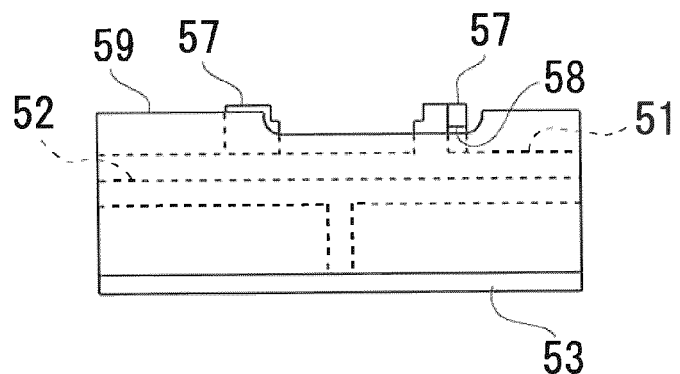

In contrast, in this example, the positioning member 50 is provided with an anti-rotation wall portion that suppresses the rotation around the axis in the direction of movement of the intraocular lens 2 at the time of detachment. FIG. 6A and FIG. 6B illustrate a positioning member 60 in this example. The positioning member 60 differs from the positioning member 50 illustrated in FIG. 4A and FIG. 4B in that anti-rotation wall portions 59 and 59 are provided on the outside of the respective side wall portions 51 and 51. The anti-rotation wall portions 59 and 59 are provided for the entire area in the front and rear direction of the positioning member 60 to be parallel to the side wall portions 51 and 51. Moreover, rib groove portions 61 and 61 configured to house a rib portion 12g of the stage portion 12 of the nozzle body 10 are formed between the side wall portion 51 and the anti-rotation wall portion 59 as described below.

FIG. 7A and FIG. 7B illustrate diagrams of the case of applying the positioning member 60 of this example to the intraocular lens insertion tool 1. Unlike FIG. 1A and FIG. 1B, it is understood that the anti-rotation wall portion 59 is disposed to be exposed to the outside of the right and left sides of the stage portion 12. Furthermore, FIG. 8A and FIG. 8B illustrate diagrams of the vicinity of the positioning member 60 in the case of applying the positioning member 60 in this example to the intraocular lens insertion tool 1. FIG. 8A illustrates the side view, and FIG. 8B illustrates an A-A cross-section thereof.

As can be seen from FIG. 8B, on the right and left lower sides of the set surface 12b in the stage portion 12 of the nozzle body 10, the rib portions 12g and 12g as the flat plate portions are provided. When the rib portion 12g is viewed from the side surface, as illustrated in FIG. 8A, the height of the leading end side thereof increases like a taper, and the rear side thereof has a constant height.

The positioning member 60 in this example is fixed in the state of housing the respective rib portions 12g between the respective side wall portions 51 and 51 and the respective anti-rotation wall portions 59 and 59, when it is mounted to the stage portion 12 from the lower side. In this example, the distance between the respective side wall portions 51 and 51 and the respective anti-rotation wall portions 59 and 59 is set to be slightly larger than the thickness of the respective rib portions 12g and 12g.

According to this, as indicated by the arrow in FIG. 8B, in a case where the user of the intraocular lens insertion tool 1 detaches the positioning member 60 from the nozzle body 10, even when trying to rotate the positioning member 60 around the axis in the front and rear direction (the axis in the direction of movement of the intraocular lens 2) of the nozzle body 10, it is possible to suppress the positioning member 60 from rotating too much. In addition, the operation of housing the rib portion 12g in the rib groove portion 61 between the side wall portion 51 and the anti-rotation wall portion 59 corresponds to the operation of suppressing the rotation of the positioning member, by causing the two wall surfaces formed parallel to the flat plate portion to face the flat plate portion from both sides in this example.

According to this, it is possible to suppress the damage of the nozzle body 10 or the positioning member 60 due to interference of the first placing portion 54 and the second placing portion 56 with the end surface of the set surface through hole 12c. Furthermore, it is possible to suppress the first placing portion 54 and the second placing portion 56 from interposing the lens main body 2a or the support portion 2b of the intraocular lens 2. Thus, it is possible to more smoothly or reliably perform the inserting operation of the intraocular lens.

In addition, it is possible to prevent a situation in which the right and left outer walls of the first positioning portions 55 and 55 of the first placing portions 54 and 54 are deformed by interference with the end surface of the set surface through hole 12c, the support portion grooves 55a and 55a collapse to close the opening portion, and the support portions 2b and 2b of the intraocular lens 2 are interposed. As a result, it is possible to prevent a situation in which the support portions 2b and 2b of the intraocular lens 2 protrude from the set surface through hole 12c, when detaching the positioning member 50.

In addition, the rotation suppressing unit in this example is configured to include the side wall portions 51 and 51, the anti-rotation wall portions 59 and 59, and the rib groove portions 61 and 61. Furthermore, in this example, the side wall portions 51 and 51, the anti-rotation wall portions 59 and 59, and the rib groove portions 61 and 61 are disposed on both sides of the intraocular lens center. Thus, the rotation suppressing unit in this example are provided on both sides with respect to the central axis in the direction of movement of the intraocular lens, when viewed from the direction of optical axis of the intraocular lens.

Second Example

Next, a second example will be described with reference to FIG. 9A and FIG. 9B. In the first example, the rib portions 12g and 12g are provided on the right and left lower sides of the set surface 12b in the stage portion 12 of the nozzle body 10, and the positioning member 60 is provided with the anti-rotation wall portions 59 and 59 on the outer side of the respective side wall portions 51 and 51. Moreover, the positioning member 60 is fixed in the state in which the respective rib portions 12g and 12g are housed between the respective side wall portions 51 and 51 and the respective anti-rotation wall portions 59 and 59, when it is attached to the stage portion 12 from the lower side.

In contrast, in this example, on the right and left lower sides of the set surface 12b in the stage portion 12 of the nozzle body 10, in addition to the rib portions 12g and 12g, anti-rotation rib portions 12h and 12h are provided inside the rib portions 12g and 12g. In addition, a positioning member 65 is not provided with the anti-rotation wall portion. Moreover, when the positioning member 65 is attached to the stage portion 12 from the lower side, it is fixed in a state in which the respective side wall portions 51 and 51 are housed in side wall groove portions 12k and 12k between the respective rib portions 12g and 12g and the respective anti-rotation rib portions 12h and 12h.

Figure 9B:
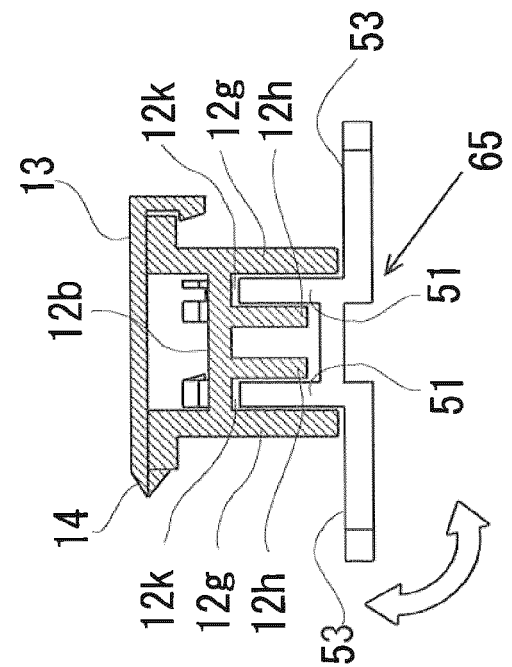
FIG. 9A and FIG. 9B are diagrams illustrating the vicinity of a positioning member in an intraocular lens insertion tool in a second example of the invention.
Figure 9A:
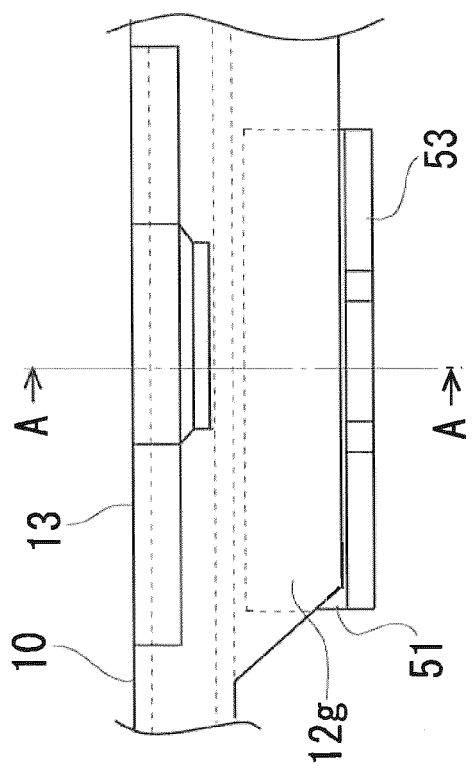

With this configuration, in a case where the user of the intraocular lens insertion tool 1 detaches the positioning member 65 from the nozzle body 10, as indicated by the arrow in FIG. 9B, even when trying to rotate the positioning member 65 around the axis in the front and rear direction (the axis in the direction of movement of the intraocular lens 2) of the nozzle body 10, it is possible to suppress the positioning member 65 from rotating too much. In addition, the operation of housing the side wall portion 51 in the side wall groove portion 12k between the rib portion 12g and the anti-rotation rib portion 12h corresponds to the operation of suppressing the rotation of the positioning member, by causing the two wall surfaces formed parallel to the flat plate portion to face the flat plate portion from both sides in this example.

Furthermore, with this configuration, it is also possible to suppress the damage of the nozzle body 10 or the positioning member 65 due to interference of the first placing portion 54 and the second placing portion 56 with the end surface of the set surface through hole 12c. Furthermore, it is possible to suppress the first placing portion 54 and the second placing portion 56 from interposing the lens main body 2a and the support portion 2b of the intraocular lens 2. Thus, it is possible to more smoothly or reliably perform the inserting operation of the intraocular lens.

In addition, it is possible to prevent the situation in which the right and left outer walls of the first positioning portions 55 and 55 of the first placing portions 54 and 54 are deformed by interference with the end surface of the set surface through holes 12c, the support portion grooves 55a and 55a collapse to close the opening portion, and the support portions 2b and 2b of the intraocular lens 2 are interposed. As a result, it is possible to prevent a situation in which the support portions 2b and 2b of the intraocular lens 2 protrude from the set surface through hole 12c, when detaching the positioning member 65.

In addition, the rotation suppressing unit in this example is configured to include the rib portions 12g and 12g, the anti-rotation rib portions 12h and 12h, and the side wall groove portions 12k and 12k.

Third Example

Next, a third example of the invention will be described. In this example, an example will be described in which, by disposing the holding portion of the positioning member on the rear side of the center in the front and rear direction of the member, while preventing the rotation about the axis in the front and rear direction of the nozzle body 10 (the direction of movement of the intraocular lens), the rotation about the axis in the leftward and rightward direction of the nozzle body 10 is allowed, and the positioning member can be more easily detached.

Figure 10A:
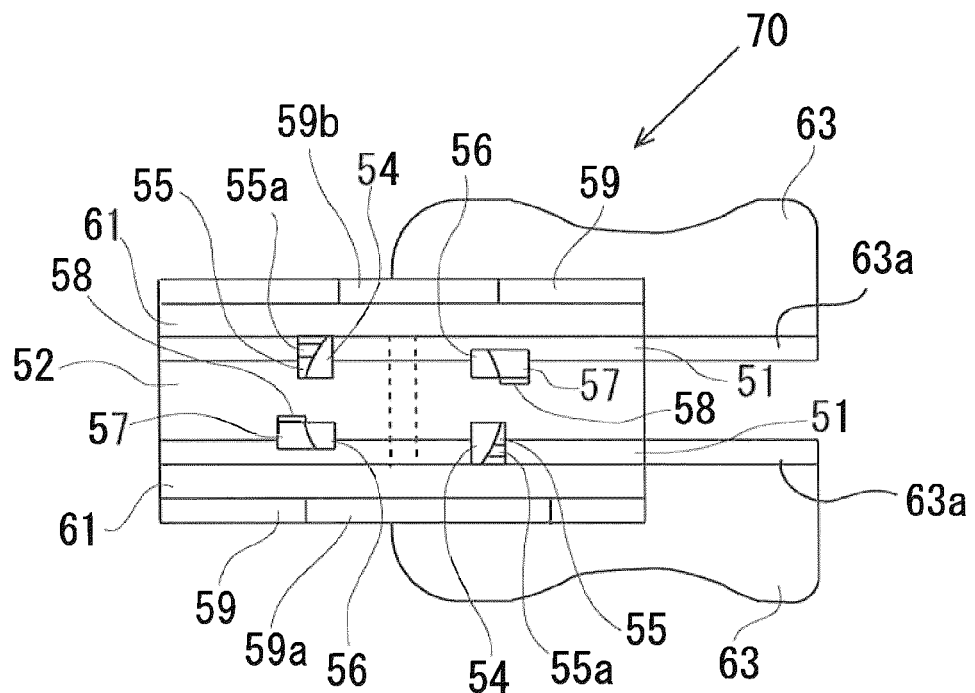
FIG. 10A and FIG. 10B are diagrams illustrating a schematic configuration of a positioning member in a third example of the invention.
Figure 10B:
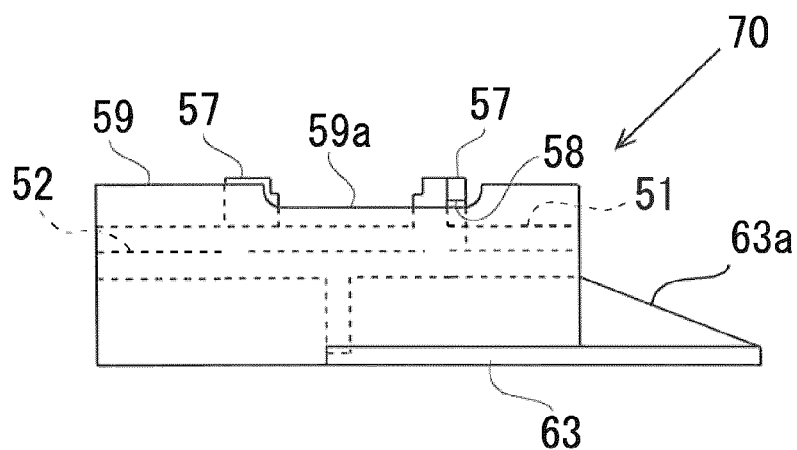

FIG. 10A and FIG. 10B illustrate a schematic configuration of a positioning member 70 in this example. FIG. 10A illustrates a plan view, and FIG. 10B illustrates a side view. Furthermore, FIG. 11A and FIG. 11B illustrate perspective views of the positioning member 70. FIG. 11A is a perspective view when viewed from the upper rear side, and FIG. 11B is a perspective view when viewed from the lower front side thereof. The positioning member 70 differs from the positioning member 60 described in FIG. 6A and FIG. 6B in that, in the positioning member 70, holding portions 63 and 63 as the gripping portions are provided so as to be biased to the rear side from the center in the front and rear direction of the positioning member 70.

FIG. 12A and FIG. 12B illustrate overall views of the case of applying the positioning member 70 of this example to the intraocular lens insertion tool 1. The locking claws 58 and 58 provided on the second positioning portions 57 and 57 as described above are locked to the top surface of the set surface 12b, and thus, the positioning member 70 is mounted to the nozzle body 10. In this example, therefore, the holding portion 63 is provided so as to be biased to the rear side from the junction of the positioning member 70 with the nozzle body 10. As a result, by simply holding and pulling the holding portion 63 downward by the user, it is possible to detach the positioning member 70 while rotating it in the direction illustrated by the arrow in FIG. 12B (around the axis in the leftward and rightward direction of the nozzle body 10), and it is possible to more easily detach the positioning member 70.

Moreover, it is possible to urge the user to rotate and detach the holding portion 63 around the axis in the leftward and rightward direction of the nozzle body 10, and it is possible to suppress the positioning member 70 from being rotated and detached around the axis in the front and rear direction of the nozzle body 10. When rotating and detaching the positioning member 70 around the axis in the horizontal direction of the nozzle body 10, since the support portion groove 55a rotates in the longitudinal direction, a risk that the support portion groove 55a collapses to interpose the support portion 2b is significantly lowered. Therefore, in this example, it is possible to more reliably or smoothly perform the inserting operation of the intraocular lens 2.

In addition, in the anti-rotation wall portions 59 and 59 of the positioning member 70 of this example, concave portions 59a and 59b are provided, respectively. Moreover, the length in the front and rear direction of the concave portion 59a is formed to be longer than the length in the front and rear direction of the concave portion 59b. This is configured so that a nozzle snap fit 13e of the lid portion 13 as illustrated in FIG. 12A and FIG. 12B can escape from the concave portion 59a but does not escape from the concave portion 59b.

According to this configuration, as illustrated in FIG. 12B, when trying to mount the positioning member 70 in a correct direction, it is possible to mount the positioning member 70 without interference between the anti-rotation wall portion 59 and the nozzle snap fit 13e. Meanwhile, when trying to mount the positioning member 70 in an incorrect direction, the anti-rotation wall portion 59 and the nozzle snap fit 13e interfere with each other and the mounting is prohibited. Thus, in the assembling process of the intraocular lens insertion tool 1, it is possible to prevent the erroneous mounting of the positioning member 70. In addition, in this example, the concave portions 59a and 59b correspond to the erroneous mounting preventing portions.

In addition, in this example, since the holding portion 63 is positioned so as to be biased to the rear side from the center in the front and rear direction of the positioning member 70, by viewing the position of the holding portion 63, it is also possible to more easily prevent the erroneous mounting of the positioning member 70.

Figure 13A:
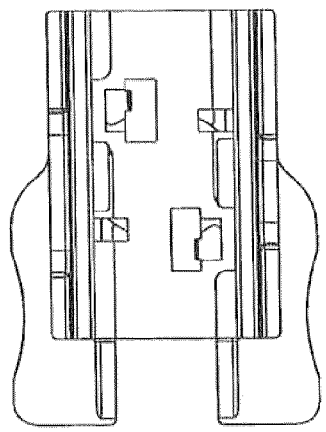
FIG. 13A to FIG. 13G are external views of the positioning member in the third example of the invention.
Figure 13B:
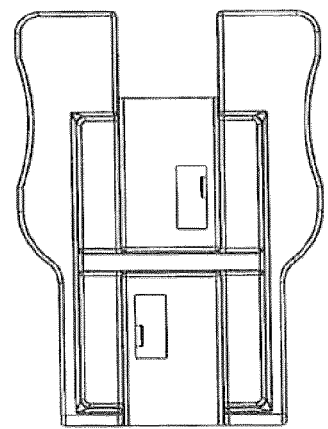
Figure 13C:
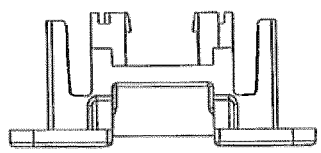
Figure 13D:
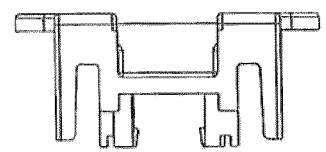
Figures 13E, 13F, 13G:
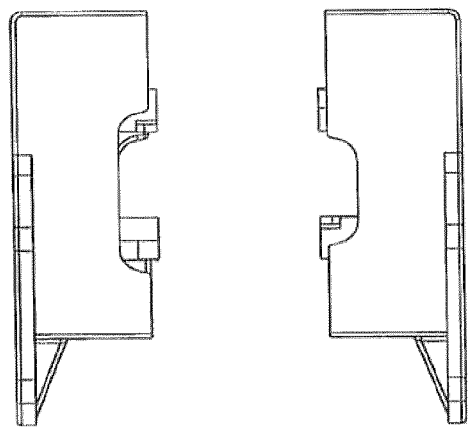

FIG. 13A to FIG. 13G are six-sided views of the positioning member 70 in this example: FIG. 13A is a plan view; FIG. 13B is a bottom view; FIG. 13C is a front view; FIG. 13D is a rear view; FIG. 13E is a left side view; FIG. 13F is a right side view; and FIG. 13G illustrates a perspective view.

Figure 14A:
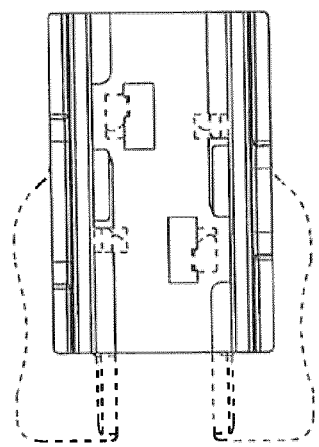
FIG. 14A to FIG. 14G are external views of the positioning member in the third example of the invention.
Figure 14B:
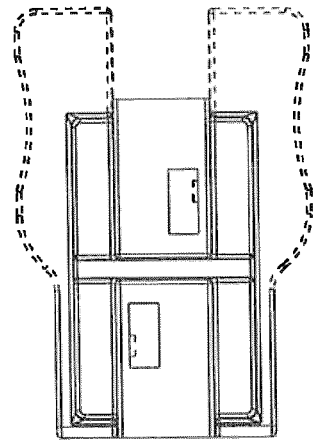
Figure 14C:
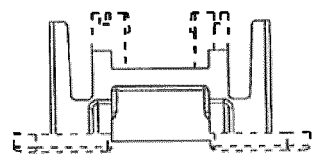
Figure 14D:
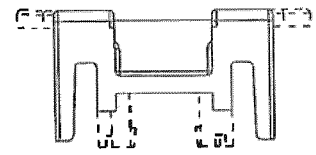
Figures 14E, 14F, 14G:
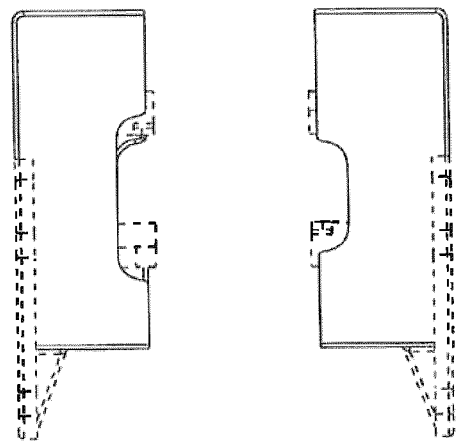

In addition, FIG. 14A to FIG. 14G illustrate characteristic portions (partial design) of an external diagram of the positioning member 70 by a solid line, and illustrates other portions by a broken line. Of course, the entire shape constituted by the characteristic portions and the broken line is also a new part, but it is to clarity the description. In FIG. 14A to FIG. 14G, FIG. 14A is a plan view; FIG. 14B is a bottom view; FIG. 14C is a front view; FIG. 14D is a rear view; FIG. 14E is a left side view; FIG. 14F is a right side view; and FIG. 14G illustrates a perspective view.

In addition, in this example, the rotation suppressing unit is configured to include the side wall portions 51 and 51, the anti-rotation wall portions 59 and 59, and the rib groove portions 61 and 61. Furthermore, in this example, the side wall portions 51 and 51, the anti-rotation wall portions 59 and 59, and the rib groove portions 61 and 61 are disposed on both sides of center of the intraocular lens. Thus, the rotation suppressing unit in this example are provided on both sides with respect to the central axis in the direction of movement of the intraocular lens, when viewed from the optical axis of the intraocular lens.

In each of the above-described examples, as the intraocular lens to be inserted, an example of using a so-called three-piece type in which the lens main body (optical portion) and the support portion are made of different materials has been described. However, it is also possible to apply the invention to an insertion tool for inserting a so-called one-piece intraocular lens in which the lens main body (optical portion) and the support portion are integrally formed. Furthermore, the shape of the positioning member is not intended to be limited to the shape of the above-described examples, unless it departs from the spirit of the invention. As long as the rotation of the positioning member is suppressed, by causing the flat plate portion formed on one of the outer circumference of the housing portion or the positioning member to be faced by the two wall surfaces formed on the other of the outer circumference of the housing portion or the positioning member from both sides, other shapes may be selected.

For example, an aspect may be adopted in which the length in the front and rear direction of the anti-rotation wall portion does not extend throughout the entire region of the positioning member, or only one anti-rotation wall portion is provided. In addition, an aspect may be adopted in which the gap between the anti-rotation wall portion and the side wall portion is smaller than the rib thickness, and the rib portion is interposed between the two wall surfaces without a gap.

In addition, the length in the front and rear direction of the anti-rotation rib portion may be equal to or different from the rib portion. Furthermore, the anti-rotation rib portion may be provided so as to be divided in the front and rear direction. In addition, only one anti-rotation rib portion may be provided. In addition, an aspect may be adopted in which the gap between the anti-rotation rib portion and the rib portion is smaller than the thickness of the side wall portion, and the side wall portion is interposed between the two wall surfaces without a gap.

REFERENCE SIGNS LIST 1 insertion tool
2 intraocular lens 10 nozzle body
10a leading end portion
10b rear end portion
10f guide portion
10g contact portion
12 stage portion
12b set surface
12g rib portion
12h anti-rotation rib portion
12k side wall groove portion
13 stage lid portion
13a rib
13b rib
13c guide projection
15 insertion cylindrical portion
30 plunger
31 acting portion
31a cylindrical portion
31b flat portion
50, 60, 70 positioning member
51 side wall portion
53, 63 holding portion
59 anti-rotation wall portion
61 rib groove portion

The invention claimed is:

1. An intraocular lens insertion tool characterized in that:
a tool main body formed in a substantially cylindrical shape that has an insertion cylindrical portion to be inserted into an incision formed in an ocular tissue, and a housing portion capable of housing and disposing an intraocular lens;
a plunger that moves the intraocular lens inside the tool main body to discharge the intraocular lens into the eyeball from the insertion cylindrical portion, by pressing the intraocular lens housed in the housing portion with a leading end, by being pushed into the tool main body; and
a positioning member that restricts an initial position and posture of the intraocular lens within the tool main body by being mounted to the housing portion from the outside,
the intraocular lens insertion tool permitting the movement of the intraocular lens and discharging into the eyeball by the plunger, by detaching the positioning member from the housing portion to release the restrictions on the position and posture of the intraocular lens within the tool main body during use,
wherein in one of an outer circumference of the housing portion or the positioning member, one or more flat plate portions configured as a flat plate-shaped wall portion formed parallel to a direction of movement of the intraocular lens and to a direction of optical axis of the intraocular lens is provided, and
in the other of the outer circumference of the housing portion or the positioning member, a rotation suppressing unit that has a first wall surface and a second wall surface formed parallel to one of the flat plate portion and suppresses the rotation of the positioning member with respect to the housing portion by causing the first wall surface to face the flat plate portion and causing the second wall surface to face a second flat surface positioned on a side opposite to the first flat surface in the flat plate portion is provided.

2. The intraocular lens insertion tool according to claim 1, wherein the one or more flat plate portions is provided on the outer circumference of the housing portion, and the rotation suppressing unit is provided in the positioning member.

3. The intraocular lens insertion tool according to claim 2, wherein the one or more flat plate portions and the rotation suppressing unit are provided on both sides with respect to a central axis in the direction of movement of the intraocular lens, when viewed from a direction of optical axis of the intraocular lens housed in the housing portion.

4. The intraocular lens insertion tool according to claim 3, wherein the positioning member has a plurality of convex portions for restricting the position of the intraocular lens, and
the plurality of convex portions is inserted into a plurality of holes formed on a placing surface as a surface on which the intraocular lens is placed in the housing portion, and when a locking portion provided on a side surface of the convex portion engages with an end surface of the placing surface forming the hole, the positioning member is mounted to the housing portion.

5. The intraocular lens insertion tool according to claim 4, wherein the intraocular lens includes a lens main body, and a whisker-like support portion extending outward from the outer circumference of the lens main body, a part of the plurality of convex portions has a groove portion for supporting the support portion, and
the groove portion is formed parallel to the direction of movement of the intraocular lens.

6. The intraocular lens insertion tool according to claim 2, wherein the positioning member has a plurality of convex portions for restricting the position of the intraocular lens, and
the plurality of convex portions is inserted into a plurality of holes formed on a placing surface as a surface on which the intraocular lens is placed in the housing portion, and when a locking portion provided on a side surface of the convex portion engages with an end surface of the placing surface forming the hole, the positioning member is mounted to the housing portion.

7. The intraocular lens insertion tool according to claim 6, wherein the intraocular lens includes a lens main body, and a whisker-like support portion extending outward from the outer circumference of the lens main body, a part of the plurality of convex portions has a groove portion for supporting the support portion, and
the groove portion is formed parallel to the direction of movement of the intraocular lens.

8. The intraocular lens insertion tool according to claim 2, wherein an erroneous mounting prevention portion is formed in at least a part of the wall surface facing the one or more flat plate portions in the rotation suppressing unit, and
the erroneous mounting prevention portion prohibits the mounting by interfering with a predetermined portion of the housing portion, when the positioning member is mounted in an opposite direction with regard to the direction of movement of the intraocular lens.

9. The intraocular lens insertion tool according to claim 1, wherein the positioning member has a plurality of convex portions for restricting the position of the intraocular lens, and
the plurality of convex portions is inserted into a plurality of holes formed on a placing surface as a surface on which the intraocular lens is placed in the housing portion, and when a locking portion provided on a side surface of the convex portion engages with an end surface of the placing surface forming the hole, the positioning member is mounted to the housing portion.

10. The intraocular lens insertion tool according to claim 9,
wherein the intraocular lens includes a lens main body, and a whisker-like support portion extending outward from the outer circumference of the lens main body,
a part of the plurality of convex portions has a groove portion for supporting the support portion, and
the groove portion is formed parallel to the direction of movement of the intraocular lens.

11. The intraocular lens insertion tool according to claim 1,
wherein the positioning member has a gripping portion for gripping when attaching or detaching the positioning member to and from the housing portion, and
the gripping portion is provided to be biased from the center in the direction of movement of the intraocular lens in the positioning member.

12. The intraocular lens insertion tool according to claim 1,
wherein the intraocular lens insertion tool is a preset type insertion tool in which the intraocular lens is housed and the positioning member is mounted in the housing portion in advance in the manufacturing process, and which is distributed in a state in which the intraocular lens is housed and the positioning member is mounted in the housing portion.

13. A positioning member provided in an intraocular lens insertion tool characterized in that:
the intraocular lens insertion tool comprising:
a tool main body formed in a substantially cylindrical shape that has an insertion cylindrical portion to be inserted into an incision formed in an ocular tissue, and a housing portion capable of housing and disposing an intraocular lens;
a plunger that moves the intraocular lens inside the tool main body to discharge the intraocular lens into the eyeball from the insertion cylindrical portion, by pressing the intraocular lens housed in the housing portion with a leading end, by being pushed into the tool main body; and
the positioning member configured to restrict an initial position and posture of the intraocular lens within the tool main body by being mounted to the housing portion from the outside,
the intraocular lens insertion tool permitting the movement of the intraocular lens and discharging into the eyeball by the plunger, by detaching the positioning member from the housing portion to release the restrictions on the position and posture of the intraocular lens within the tool main body during use,
wherein in one of an outer circumference of the housing portion or the positioning member, one or more flat plate portions configured as a flat plate-shaped wall portion formed parallel to a direction of movement of the intraocular lens and to a direction of optical axis of the intraocular lens is provided, and
in the other of the outer circumference of the housing portion or the positioning member, a rotation suppressing unit that has a first wall surface and a second wall surface formed parallel to one of the flat plate portion and suppresses the rotation of the positioning member with respect to the housing portion by causing the first wall surface to face the flat plate portion and causing the second wall surface to face a second flat surface positioned on a side opposite to the first flat surface in the flat plate portion is provided; wherein the positioning member has a gripping portion for gripping when attaching or detaching the positioning member to and from the housing portion, and the gripping portion is provided to be biased from the center in the direction of movement of the intraocular lens in the positioning member.

14. The positioning member according to claim 13, wherein the one or more flat plate portions is provided on the outer circumference of the housing portion, and the rotation suppressing unit is provided in the positioning member.

15. The positioning member according to claim 14,
wherein an erroneous mounting prevention portion is formed in at least a part of the wall surface facing the one or more flat plate portions in the rotation suppressing unit, and
the erroneous mounting prevention portion prohibits the mounting by interfering with a predetermined portion of the housing portion, when the positioning member is mounted in an opposite direction with regard to the direction of movement of the intraocular lens.

16. The positioning member according to claim 13,
wherein the positioning member has a plurality of convex portions for restricting the position of the intraocular lens, and
the plurality of convex portions is inserted into a plurality of holes formed on a placing surface as a surface on which the intraocular lens is placed in the housing portion, and when a locking portion provided on a side surface of the convex portion engages with an end surface of the placing surface forming the hole, the positioning member is mounted to the housing portion.

17. The positioning member according to claim 16,
wherein the intraocular lens includes a lens main body, and a whisker-like support portion extending outward from the outer circumference of the lens main body,
a part of the plurality of convex portions has a groove portion for supporting the support portion, and
the groove portion is formed parallel to the direction of movement of the intraocular lens.

18. The positioning member according to claim 13,
wherein the intraocular lens insertion tool is a preset type insertion tool in which the intraocular lens is housed and the positioning member is mounted in the housing portion in advance in the manufacturing process, and which is distributed in a state in which the intraocular lens is housed and the positioning member is mounted in the housing portion.

* * * * *